United States Patent
Wang et al.

(10) Patent No.: US 10,301,562 B2
(45) Date of Patent: *May 28, 2019

(54) APPARATUS EXPOSABLE IN BYPRODUCE CARCONACEOUS MATERIAL FORMATION ENVIRONMENT AND ASSOCIATED METHOD

(71) Applicant: General Electric Company, Schenectady, NY (US)

(72) Inventors: Shizhong Wang, Shanghai (CN); Wenqing Peng, Shanghai (CN); Lawrence Bernard Kool, Clifton Park, NY (US); Nan Hao, Shanghai (CN); Wusheng Xu, Shanghai (CN); Minghu Guo, Shanghai (CN); Hong Zhou, Shanghai (CN); Yanfei Gu, Shanghai (CN); Zhaohui Yang, Shanghai (CN)

(73) Assignee: General Electric Company, Schenectady, NY (US)

( * ) Notice: Subject to any disclaimer, the term of this patent is extended or adjusted under 35 U.S.C. 154(b) by 28 days.

This patent is subject to a terminal disclaimer.

(21) Appl. No.: 15/103,904

(22) PCT Filed: Nov. 4, 2014

(86) PCT No.: PCT/US2014/063771
§ 371 (c)(1),
(2) Date: Jun. 13, 2016

(87) PCT Pub. No.: WO2015/088671
PCT Pub. Date: Jun. 18, 2015

(65) Prior Publication Data
US 2016/0312135 A1  Oct. 27, 2016

(30) Foreign Application Priority Data
Dec. 13, 2013  (CN) .......................... 2013 1 0686812

(51) Int. Cl.
*B01J 19/00* (2006.01)
*B01J 19/02* (2006.01)
(Continued)

(52) U.S. Cl.
CPC .............. *C10G 75/00* (2013.01); *B01J 19/02* (2013.01); *C01G 25/006* (2013.01);
(Continued)

(58) Field of Classification Search
CPC ... B01J 19/00; B01J 19/02; B01J 19/24; B01J 2219/02; B01J 2219/0204;
(Continued)

(56) References Cited

U.S. PATENT DOCUMENTS 4,454,021 A   6/1984  Watanabe et al.
6,410,171 B1  6/2002  Paulson
(Continued)

FOREIGN PATENT DOCUMENTS

EP      1118383 A1 *  7/2001  ............ B01J 23/002
WO   2005049224 A1    6/2005
WO   2012087550 A1    6/2012

OTHER PUBLICATIONS

Pietri, et al., "CO2 Reforming of Methane on LaA'Ru0.8Ni0.2O3(A'= Sm, Nd, Ca) perovskites as catalysts Precursors in presence and absence of O2", Prepr. Pap.Am. Chem. Soc., Div. Fuel Chem., Date: 2004,p. (134).
(Continued)

*Primary Examiner* — Natasha E Young
(74) *Attorney, Agent, or Firm* — Wegman, Hessler & Vanderburg

(57) ABSTRACT

An apparatus has a surface exposable to a byproduct carbonaceous material formation environment and comprising a perovskite material having an $ABO_3$ perovskite structure and being of formula $A_aB_bO_{3-\delta}$, wherein $0.9 < a \leq 1.2$;
(Continued)

$0.9 < b \leq 1.2$; $-0.5 < \delta < 0.5$; A is a combination of a first element and a second element, the first element is selected from yttrium, bismuth, lanthanum, cerium, praseodymium, neodymium, promethium, samarium, europium, gadolinium, terbium, dysprosium, holmium, erbium, thulium, ytterbium, lutetium and any combination thereof, the second element is selected from calcium, strontium, barium, lithium, sodium, potassium, rubidium and any combination thereof; and B is selected from silver, gold, cadmium, cerium, cobalt, chromium, copper, dysprosium, erbium, europium, ferrum, gallium, gadolinium, hafnium, holmium, indium, iridium, lanthanum, lutetium, manganese, molybdenum, niobium, neodymium, nickel, osmium, palladium, promethium, praseodymium, platinum, rhenium, rhodium, ruthenium, antimony, scandium, samarium, tin, tantalum, terbium, technetium, titanium, thulium, vanadium, tungsten, yttrium, ytterbium, zinc, zirconium, and any combination thereof. An associated method is also described.

5 Claims, 1 Drawing Sheet

(51) Int. Cl.

| | | |
|---|---|---|
| *B01J 19/24* | (2006.01) | |
| *C01G 25/00* | (2006.01) | |
| *C01G 29/00* | (2006.01) | |
| *C07C 4/02* | (2006.01) | |
| *C09D 1/00* | (2006.01) | |
| *C09D 7/00* | (2018.01) | |
| *C10G 9/16* | (2006.01) | |
| *C10G 9/20* | (2006.01) | |
| *C10G 75/00* | (2006.01) | |
| *C10G 9/00* | (2006.01) | |

(52) U.S. Cl.
CPC .............. *C01G 29/006* (2013.01); *C07C 4/02* (2013.01); *C09D 1/00* (2013.01); *C09D 7/00* (2013.01); *C10G 9/00* (2013.01); *C10G 9/16* (2013.01); *C10G 9/203* (2013.01); *B01J 2219/024* (2013.01); *C10G 2300/4075* (2013.01)

(58) Field of Classification Search
CPC ........ B01J 2219/0236; B01J 2219/024; C01G 25/00; C01G 25/006; C01G 29/00; C01G 29/006; C07C 4/00; C07C 4/02; C09D 1/00; C09D 7/00; C10G 9/00; C10G 9/14–203; C10G 75/00; C10G 2300/00; C10G 2300/40; C10G 2300/4075
See application file for complete search history.

(56) References Cited

U.S. PATENT DOCUMENTS

| | | | |
|---|---|---|---|
| 6,864,213 B2 | 3/2005 | LaBarge et al. | |
| 7,723,257 B2 | 5/2010 | Bosteels | |
| 8,173,010 B2 | 5/2012 | Ying et al. | |
| 8,999,878 B2* | 4/2015 | Takeshima | B01D 53/945 502/241 |
| 2004/0188323 A1 | 9/2004 | Tzatzov et al. | |
| 2007/0260101 A1 | 11/2007 | Carrera et al. | |
| 2009/0098289 A1 | 4/2009 | Deininger et al. | |
| 2010/0112408 A1* | 5/2010 | Yang | C01G 25/006 429/489 |
| 2011/0295051 A1 | 12/2011 | Wang et al. | |
| 2016/0122886 A1* | 5/2016 | Wang | B01D 53/326 205/551 |
| 2016/0304796 A1* | 10/2016 | Wang | C23C 24/082 |
| 2016/0369174 A1* | 12/2016 | Kool | B01J 19/02 |
| 2017/0001913 A1* | 1/2017 | Zhou | B01J 37/0225 |

OTHER PUBLICATIONS

Azimova, et al. "Transport properties and stability of cobalt doped proton conducting oxides", Solid State Ionics, P Date: 2009, pp. (01-08).

* cited by examiner

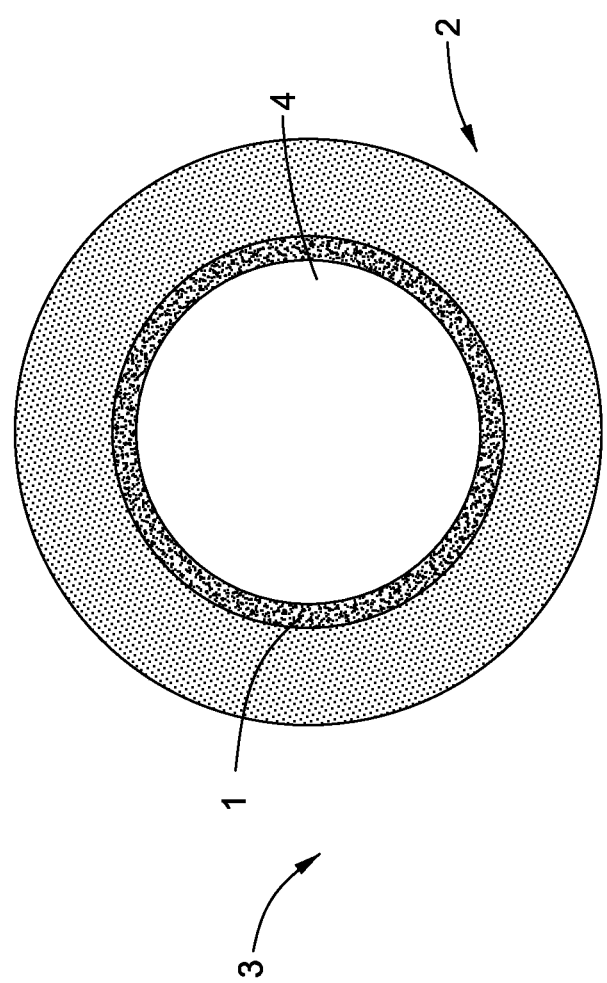

APPARATUS EXPOSABLE IN BYPRODUCE CARCONACEOUS MATERIAL FORMATION ENVIRONMENT AND ASSOCIATED METHOD

CROSS-REFERENCE TO RELATED APPLICATIONS

This application claims the priority filing benefit of International Application No. PCT/US2014/063771, filed Nov. 4, 2014, which claims the benefit of Chinese Patent Application No. CN 201310686812, filed Dec. 13, 2013, the entire contents of which are hereby incorporated herein by reference.

BACKGROUND

Embodiments of the invention relate generally to apparatuses exposable in byproduct carbonaceous material formation environments with zero or reduced build-up of byproduct carbonaceous material, and associated methods.

Byproduct carbonaceous materials of many processes are usually undesirable. For example, during hydrocarbon cracking processes, the build-up of the byproduct carbonaceous materials (e.g. coke) happens on inner surfaces of apparatus components, for instance, inner radiant tube surfaces of furnace equipment. When the inner radiant tube surfaces become gradually coated with a layer of coke, the radiant tube metal temperature (TMT) rises and the pressure drop through radiant coils increases. In addition, the byproduct carbonaceous material build-up adversely affects the physical characteristics of the apparatus components, e.g., the radiant tubes, by deteriorating mechanical properties such as stress rupture, thermal fatigue, and ductility due to carburization.

Other byproduct carbonaceous material formation apparatuses and methods, e.g., apparatuses and methods for the steam reforming of methane and for carbonaceous fuel combustion, also have problems caused by the build-up of byproduct carbonaceous material.

A variety of methods have been considered in order to overcome the disadvantages of byproduct carbonaceous material build-up on apparatus components, such as furnace tube inner surfaces. These methods include: metallurgy upgrade to alloys with increased chromium content of the metal substrates used in the apparatuses; and adding additives such as sulfur, dimethyl sulfide (DMS), and dimethyl disulfide (DMDS) or hydrogen sulfide to the feedstock to the apparatuses.

While some of the aforementioned methods have general use in some industries, it is desirable to provide new apparatuses and associated methods with zero or reduced build-up of byproduct carbonaceous material.

BRIEF DESCRIPTION

In one aspect, the invention relates to an apparatus having a surface exposable to a byproduct carbonaceous material formation environment, the surface comprising a perovskite material having a $ABO_3$ perovskite structure and being of formula $A_aB_bO_{3-\delta}$, wherein $0.9<a\leq1.2$; $0.9<b\leq1.2$; $-0.5<\delta<0.5$; A comprises a combination of a first element and a second element, the first element is selected from yttrium (Y), bismuth (Bi), cerium (Ce), lanthanum (La), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu) and any combination thereof, the second element is selected from calcium (Ca), strontium (Sr), barium (Ba), lithium (Li), sodium (Na), potassium (K), rubidium (Rb) and any combination thereof; and B is selected from silver (Ag), gold (Au), cadmium (Cd), cerium (Ce), cobalt (Co), chromium (Cr), copper (Cu), dysprosium (Dy), erbium (Er), europium (Eu), ferrum (Fe), gallium (Ga), gadolinium (Gd), hafnium (Hf), holmium (Ho), indium (In), iridium (Ir), lanthanum (La), lutetium (Lu), manganese (Mn), molybdenum (Mo), niobium (Nb), neodymium (Nd), nickel (Ni), osmium (Os), palladium (Pd), promethium (Pm), praseodymium (Pr), platinum (Pt), rhenium (Re), rhodium (Rh), ruthenium (Ru), antimony (Sb), scandium (Sc), samarium (Sm), tin (Sn), tantalum (Ta), terbium (Tb), technetium (Tc), titanium (Ti), thulium (Tm), vanadium (V), tungsten (W), yttrium (Y), ytterbium (Yb), zinc (Zn), zirconium (Zr), and any combination thereof.

In another aspect, the invention relates to a method, comprising: providing the apparatus described in the paragraph above; and exposing the surface to a byproduct carbonaceous material formation environment.

BRIEF DESCRIPTION OF THE DRAWINGS

These and other features, aspects, and advantages of the present invention will become better understood when the following detailed description is read with reference to the accompanying drawings, wherein:

FIG. 1 illustrates a schematic cross sectional view of a tube of an apparatus according to some embodiments of the invention.

DETAILED DESCRIPTION

Unless defined otherwise, technical and scientific terms used herein have the same meaning as is commonly understood by one of ordinary skill in the art to which this disclosure belongs. The use of "including", "comprising" or "having" and variations thereof herein are meant to encompass the items listed thereafter and equivalents thereof as well as additional items.

Approximating language, as used herein throughout the specification and claims, may be applied to modify any quantitative representation that could permissibly vary without resulting in a change in the basic function to which it is related. Accordingly, a value modified by a term or terms, such as "about" is not to be limited to the precise value specified. In some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

In the specification and the claims, the singular forms "a", "an" and "the" include plural referents unless the context clearly dictates otherwise. Moreover, the suffix "(s)" as used herein is usually intended to include both the singular and the plural of the term that it modifies, thereby including one or more of that term.

As used herein, the term "or" is not meant to be exclusive and refers to at least one of the referenced components (for example, a material) being present and includes instances in which a combination of the referenced components may be present, unless the context clearly dictates otherwise.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. For example, in some circumstances, an event or capacity can be expected, while in other circumstances, the event or capacity cannot occur. This distinction is captured by the terms "may" and "may be".

Reference throughout the specification to "some embodiments", and so forth, means that a particular element (e.g., feature, structure, and/or characteristic) described in connection with the invention is included in at least one embodiment described herein, and may or may not be present in other embodiments. In addition, it is to be understood that the described inventive features may be combined in any suitable manner in the various embodiments.

Embodiments of the present invention relate to apparatuses and associated methods with zero or reduced build-up of byproduct carbonaceous material in byproduct carbonaceous material formation environments.

As used herein, the term "apparatus" refers to any device that may be exposed to a byproduct carbonaceous material formation environment. In some embodiments, the apparatus includes a furnace tube, a tube fitting, a reaction vessel, a radiant tube, or any combination thereof. The apparatus may be a pyrolysis furnace comprising a firebox through which runs an array of tubing. The array of tubing and corresponding fittings may be several hundred meters in length. The array of tubing may comprise straight or serpentine tubes.

As used herein the term "byproduct carbonaceous material" refers to but is not limited to carbonaceous solid or liquid, or particulates or macromolecules forming the carbonaceous solid or liquid, which are derived from coal, petroleum, wood, hydrocarbons and other materials containing carbon and which include, for example, carbon black, tar, coke, or any combination thereof.

As used herein, the term "byproduct carbonaceous material formation environment" refers to any environments that may yield carbonaceous material as an undesirable byproduct. In some embodiments, the byproduct formation environment is a petrochemical processing environment. In some embodiments, the byproduct carbonaceous material formation environment is hydrocarbon cracking environment.

In some embodiments, the byproduct carbonaceous material formation environment is a hydrocarbon cracking environment at a temperature in a range from about 700° C. to about 900° C., a weight ratio of steam to hydrocarbon is in a range from about 3:7 to about 7:3, and the hydrocarbon comprises ethane, heptane, liquid petroleum gas, naphtha, gas oil, or any combination thereof.

In some embodiments, the byproduct carbonaceous material formation environment is a hydrocarbon cracking environment at a temperature in a range from about 480° C. to about 600° C., and the hydrocarbon comprises bottoms from atmospheric and vacuum distillation of crude oil and a weight percentage of steam is in a range from about 1 wt % to about 2 wt %.

As used herein the term "hydrocarbon cracking", "cracking hydrocarbon", or any variation thereof, refers to but is not limited to processes in which hydrocarbons such as ethane, propane, butane, naphtha, bottoms from atmospheric and vacuum distillation of crude oil are cracked in apparatuses to obtain materials with smaller molecules.

As used herein the term "perovskite material" or any variation thereof refers to any material having an $ABO_3$ perovskite structure and being of formula $A_aB_bO_{3-\delta}$. In some embodiments, in the $ABO_3$ perovskite structure, A cations are surrounded by twelve anions in cubo-octahedral coordination, B cations are surrounded by six anions in octahedral coordination, and oxygen anions are coordinated by two B cations and four A cations. In some embodiments, the $ABO_3$ perovskite structure is built from corner-sharing $BO_6$ octahedra. In some embodiments, the $ABO_3$ perovskite structure includes distorted derivatives. The distortions may be due to rotation or tilting of regular, rigid octahedra or due to the presence of distorted $BO_6$ octahedra. In some embodiments, the $ABO_3$ perovskite structure is cubic. In some embodiments, the $ABO_3$ perovskite structure is hexagonal.

In some embodiments, the perovskite material may be of formula $n(A_aB_bO_{3-\delta})$, in which n=1, 2, 3, 4, 8, and etc.

The first element may be a single element or a combination of elements, selected from yttrium (Y), bismuth (Bi), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

The second element may be a single element or a combination of elements, selected from calcium (Ca), strontium (Sr), barium (Ba), lithium (Li), sodium (Na), potassium (K), and rubidium (Rb).

Likewise, B may be a single element or a combination of elements selected from silver (Ag), gold (Au), cadmium (Cd), cerium (Ce), cobalt (Co), chromium (Cr), copper (Cu), dysprosium (Dy), erbium (Er), europium (Eu), ferrum (Fe), gallium (Ga), gadolinium (Gd), hafnium (Hf), holmium (Ho), indium (In), iridium (Ir), lanthanum (La), lutetium (Lu), manganese (Mn), molybdenum (Mo), niobium (Nb), neodymium (Nd), nickel (Ni), osmium (Os), palladium (Pd), promethium (Pm), praseodymium (Pr), platinum (Pt), rhenium (Re), rhodium (Rh), ruthenium (Ru), antimony (Sb), scandium (Sc), samarium (Sm), tin (Sn), tantalum (Ta), terbium (Tb), technetium (Tc), titanium (Ti), thulium (Tm), vanadium (V), tungsten (W), yttrium (Y), ytterbium (Yb), zinc (Zn), and zirconium (Zr).

In some embodiments, the perovskite material comprises $La_{0.1}Ba_{0.9}Ce_{0.7}Zr_{0.2}Y_{0.1}O_3$, $Ce_{0.1}Ba_{0.9}Ce_{0.7}Zr_{0.2}Y_{0.1}O_{3.05}$, $Ce_{0.5}Ba_{0.5}Ce_{0.7}Zr_{0.2}Y_{0.1}O_{3.45}$, $Y_{0.1}Ba_{0.9}Ce_{0.7}Zr_{0.2}Y_{0.1}O_3$, $Y_{0.5}Ba_{0.5}Ce_{0.7}Zr_{0.2}Y_{0.1}O_{3.2}$, $Bi_{0.1}Ba_{0.9}Ce_{0.7}Zr_{0.2}Y_{0.1}O_3$, $Bi_{0.5}Ba_{0.5}Ce_{0.7}Zr_{0.2}Y_{0.1}O_{3.2}$, $Pr_{0.1}Ba_{0.9}Ce_{0.7}Zr_{0.2}Y_{0.1}O_3$, $Pr_{0.5}Ba_{0.5}Ce_{0.7}Zr_{0.2}Y_{0.1}O_{3.2}$, or any combination thereof. For $La_{0.1}Ba_{0.9}Ce_{0.7}Zr_{0.2}Y_{0.1}O_3$, A is a combination of Ba and La, the first element is La, the second element is Ba, a=1, B is a combination of Ce, Zr and Y, b=1, and, $\delta$=0. For $Ce_{0.1}Ba_{0.9}Ce_{0.7}Zr_{0.2}Y_{0.1}O_{3.05}$ and $Ce_{0.5}Ba_{0.5}Ce_{0.7}Zr_{0.2}Y_{0.1}O_{3.45}$, A is a combination of Ce and Ba, the first element is Ce, the second element is Ba, a=1, B is a combination of Ce, Zr and Y, b=1, and, $\delta$=−0.05 and −0.45, respectively. For $Y_{0.1}Ba_{0.9}Ce_{0.7}Zr_{0.2}Y_{0.1}O_3$ and $Y_{0.5}Ba_{0.5}Ce_{0.7}Zr_{0.2}Y_{0.1}O_{3.2}$, A is a combination of Y and Ba, the first element is Y, the second element is Ba, a=1, B is a combination of Ce, Zr and Y, b=1, and, $\delta$=0 and −0.2, respectively. For $Bi_{0.1}Ba_{0.9}Ce_{0.7}Zr_{0.2}Y_{0.1}O_3$ and $Bi_{0.5}Ba_{0.5}Ce_{0.7}Zr_{0.2}Y_{0.1}O_{3.2}$, A is a combination of Bi and Ba, the first element is Bi, the second element is Ba, a=1, B is a combination of Ce, Zr and Y, b=1, and, $\delta$=0 and −0.2, respectively. Similarly, for $Pr_{0.1}Ba_{0.9}Ce_{0.7}Zr_{0.2}Y_{0.1}O_3$ and $Pr_{0.5}Ba_{0.5}Ce_{0.7}Zr_{0.2}Y_{0.1}O_{3.2}$, A is a combination of Pr and Ba, the first element is Pr, the second element is Ba, a=1, B is a combination of Ce, Zr and Y, b=1, and, δ=0 and −0.2, respectively.

As can be seen from examples herein, the perovskite material comprising a combination of the first element and the second element in the A site is stable and anticoking in the byproduct carbonaceous material formation environment. Therefore, when at least one of the perovskite material is in the surface of the apparatus exposed to the byproduct carbonaceous material formation environment, the build-up of byproduct carbonaceous material on the surface is avoided or reduced.

In some embodiments, as is shown in FIG. 1, the surface 1 is an inner surface of a tube 2 of an apparatus 3, and the byproduct carbonaceous material formation environment 4 is inside the tube 2.

In some embodiments, the surface of the apparatus exposed to the byproduct carbonaceous material formation environment comprises a coating of the perovskite material. The perovskite material may be coated to the surface of the apparatus using different methods, for example, air plasma spray, slurry coating, sol-gel coating, solution coating, or any combination thereof.

In some embodiments, the perovskite material is slurry coated. The slurry may further comprise an organic binder, an inorganic binder, a wetting agent, a solvent or any combination thereof to enhance the slurry wetting ability, tune the slurry viscosity or get a good green coating strength. When the organic binder, the inorganic binder, the wetting agent, the solvent, or any combination thereof is added in the slurry, a total weight percentage of the perovskite material in the slurry may be from about 10% to about 90%, or from about 15% to about 70%, or more particularly from about 30% to about 55%.

The slurry may be applied by different techniques, such as sponging, painting, centrifuging, spraying, filling and draining, dipping, or any combination thereof. In some embodiments, the slurry is applied by dipping, i.e., dipping the part of the apparatus to be coated in the slurry. In some embodiments, the slurry is applied by filling and draining, i.e., filling the slurry in the tube of the apparatus to be coated and draining out the slurry afterwards by, e.g., gravity.

In some embodiments, after the slurry is applied to the surface of the apparatus, the coated apparatus is sintered to obtain a coating with a good strength at a high temperature. As used herein the term "sintering" or any variations thereof refers to, but is not limited to, a method of heating the material in a sintering furnace or other heater facility. In some embodiments, the sintering temperature is in a range from about 850° C. to about 1000° C. In some embodiments, the sintering temperature is about 1000° C.

EXAMPLES

The following examples are included to provide additional guidance to those of ordinary skill in the art in practicing the claimed invention. These examples do not limit the invention as defined in the appended claims.

Example 1 Perovskite Material Preparation

The perovoskite material was prepared by solid-state reaction method. Stoichiometric amounts of high-purity barium carbonate, zirconium oxide, lanthanum oxide, yttrium oxide, bismuth oxide, praseodymium oxide and cerium oxide powders (all from sinopharm chemical reagent Co., Ltd. (SCRC), Shanghai, China) were mixed and calcined at 1600° C. in air for 6 hours to form the powders of $La_{0.1}Ba_{0.9}Ce_{0.7}Zr_{0.2}Y_{0.1}O_3$, $Ce_{0.1}Ba_{0.9}Ce_{0.7}Zr_{0.2}Y_{0.1}O_{3.05}$, $Ce_{0.5}Ba_{0.5}Ce_{0.7}Zr_{0.2}Y_{0.1}O_{3.45}$, $Y_{0.1}Ba_{0.9}Ce_{0.7}Zr_{0.2}Y_{0.1}O_3$, $Y_{0.5}Ba_{0.5}Ce_{0.7}Zr_{0.2}Y_{0.1}O_{3.2}$, $Bi_{0.1}Ba_{0.9}Ce_{0.7}Zr_{0.2}Y_{0.1}O_3$, $Bi_{0.5}Ba_{0.5}Ce_{0.7}Zr_{0.2}Y_{0.1}O_{3.2}$, $Pr_{0.1}Ba_{0.9}Ce_{0.7}Zr_{0.2}Y_{0.1}O_3$, and $Pr_{0.5}Ba_{0.5}Ce_{0.7}Zr_{0.2}Y_{0.1}O_{3.2}$, respectively.

X-ray diffraction (XRD) analyses were conducted to examine the crystal structures of the materials. Perovskite structures were observed in all of the materials and 2 theta angles of all the materials were increased with respect to $BaCe_{0.7}Zr_{0.2}Y_{0.1}O_3$, indicating lanthanum, cerium, yttrium, bismuth, and praseodymium respectively replaced some of barium in the $BaCe_{0.7}Zr_{0.2}Y_{0.1}O_3$ crystal structure and coexisted with barium in the A site of the perovskite material.

Example 2 Hydrocarbon Cracking $La_{0.1}Ba_{0.9}Ce_{0.7}Zr_{0.2}Y_{0.1}O_3$ powders prepared in example 1 were molded into bars which were placed at the constant temperature region of a lab scale hydrocarbon-cracking furnace. The furnace door was then closed. Argon gas was fed in the furnace at the flow rate of 100 standard cubic centimeters per minute (sccm). The cracking furnace was heated to 850° C. with the ramping rate of 20° C./min. A vaporizer was heated to 350° C. within 30 minutes.

When the temperature of the cracking furnace reached 850° C. and the temperature of the vaporizer reached 350° C., water was pumped using a piston pump into the vaporizer with the flow rate of 1.58 ml/min. Argon gas feeding was stopped. After 5 minutes, heptane was pumped using a piston pump into the vaporizer with the flow rate of 2.32 ml/min to be vaporized and mixed with the steam in the vaporizer in a 1:1 weight ratio. The temperature of the cracking furnace was maintained at desired temperature, e.g., 850+/−5° C. for 2 hours before stopping the pumpings of the heptane and water. The residence time of the heptane and steam in the cracking furnace was 1.5 seconds. Argon gas was fed again at the flow rate of 100 sccm before the cracking furnace and the vaporizer were shut down. When the cracking furnace cooled down, argon gas feed was stopped and the furnace door was opened to take out the sample holders.

No coke was observed on any of the bars and XRD analysis showed that the crystal structure did not change with respect to before hydrocarbon cracking, indicating the perovskite material of formula $La_{0.1}Ba_{0.9}Ce_{0.7}Zr_{0.2}Y_{0.1}O_3$ is anticoking and stable in the byproduct carbonaceous material formation environment.

While only certain features of the invention have been illustrated and described herein, many modifications and changes will occur to those skilled in the art. It is, therefore, to be understood that the appended claims are intended to cover all such modifications and changes as fall within the true spirit of the invention.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A method, comprising:
providing an apparatus having a surface exposable to a byproduct carbonaceous material formation environment, the surface comprising a perovskite material having an $ABO_3$ perovskite structure and being of formula $A_aB_bO_{3-\delta}$, wherein

$0.9<a\leq1.2$;

$0.9<b\leq1.2$;

$-0.5<\delta<0.5$;

A is a combination of a first element and a second element, the first element is selected from yttrium (Y), bismuth (Bi), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu) and any combination thereof, the second element is selected from calcium (Ca), strontium (Sr), barium (Ba), lithium (Li), sodium (Na), potassium (K), rubidium (Rb) and any combination thereof;

B is selected from silver (Ag), gold (Au), cadmium (Cd), cerium (Ce), cobalt (Co), chromium (Cr), copper (Cu), dysprosium (Dy), erbium (Er), europium (Eu), ferrum (Fe), gallium (Ga), gadolinium (Gd), hafnium (Hf), holmium (Ho), indium (In), iridium (Ir), lanthanum (La), lutetium (Lu), manganese (Mn), molybdenum (Mo), niobium (Nb), neodymium (Nd), nickel (Ni), osmium (Os), palladium (Pd), promethium (Pm), praseodymium (Pr), platinum (Pt), rhenium (Re), rhodium (Rh), ruthenium (Ru), antimony (Sb), scandium (Sc), samarium (Sm), tin (Sn), tantalum (Ta), terbium (Tb), technetium (Tc), titanium (Ti), thulium (Tm), vanadium (V), tungsten (W), yttrium (Y), ytterbium (Yb), zinc (Zn), zirconium (Zr), and any combination thereof, wherein the surface comprises a coating of the perovskite material; and exposing the surface to a byproduct carbonaceous material formation environment, wherein the byproduct carbonaceous material formation environment is a hydrocarbon cracking environment.

2. The method of claim 1, wherein the perovskite material is of formula $La_{0.1}Ba_{0.9}Ce_{0.7}Zr_{0.2}Y_{0.1}O_3$, $Ce_{0.1}Ba_{0.9}Ce_{0.7}Zr_{0.2}Y_{0.1}O_{3.05}$, $Ce_{0.5}Ba_{0.5}Ce_{0.7}Zr_{0.2}Y_{0.1}O_{3.45}$, $Y_{0.1}Ba_{0.9}Ce_{0.7}Zr_{0.2}Y_{0.1}O_3$, $Y_{0.5}Ba_{0.5}Ce_{0.7}Zr_{0.2}Y_{0.1}O_{3.2}$, $Bi_{0.1}Ba_{0.9}Ce_{0.7}Zr_{0.2}Y_{0.1}O_3$, $Bi_{0.5}Ba_{0.5}Ce_{0.7}Zr_{0.2}Y_{0.1}O_{3.2}$, $Pr_{0.1}Ba_{0.9}Ce_{0.7}Zr_{0.2}Y_{0.1}O_3$, or $Pr_{0.5}Ba_{0.5}Ce_{0.7}Zr_{0.2}Y_{0.1}O_{3.2}$.

3. The method of claim 1, wherein the hydrocarbon comprises ethane, heptane, liquid petroleum gas, naphtha, gas oil, or any combination thereof.

4. The method of claim 1, wherein the surface is an inner surface of a tube.

5. The method of claim 1, wherein the surface comprises a coating of the perovskite material.

* * * * *